(12) United States Patent
Ahmed et al.

(10) Patent No.: US 7,496,394 B2
(45) Date of Patent: Feb. 24, 2009

(54) INTERNAL REFERENCE CORONARY SINUS CATHETER

(75) Inventors: Naseeruddin Ahmed, Karachi (PK); Shiva Sharareh, Laguna Niguel, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 178 days.

(21) Appl. No.: 10/990,145

(22) Filed: Nov. 15, 2004

(65) Prior Publication Data

US 2006/0106298 A1 May 18, 2006

(51) Int. Cl.
*A61B 5/04* (2006.01)
*A61B 18/14* (2006.01)

(52) U.S. Cl. ........................ 600/381; 606/41
(58) Field of Classification Search .................. 600/374, 600/381; 606/41
See application file for complete search history.

(56) References Cited

U.S. PATENT DOCUMENTS

| | | | |
|---|---|---|---|
| 5,221,261 A * | 6/1993 | Termin et al. ................ | 604/104 |
| 5,465,717 A | 11/1995 | Imran et al. | |
| 5,954,761 A * | 9/1999 | Machek et al. ............... | 607/126 |
| 6,161,029 A * | 12/2000 | Spreigl et al. ................ | 600/381 |
| 6,500,174 B1 | 12/2002 | Maguire et al. | |
| 6,529,756 B1 | 3/2003 | Phan et al. | |
| 6,602,242 B1 * | 8/2003 | Fung et al. ................... | 604/528 |
| 6,949,097 B2 * | 9/2005 | Stewart et al. ................ | 606/41 |
| 7,039,450 B2 * | 5/2006 | Duarte ........................ | 600/374 |
| 7,107,105 B2 * | 9/2006 | Bjorklund et al. ........... | 607/126 |

FOREIGN PATENT DOCUMENTS

| | | |
|---|---|---|
| EP | 1 319 365 A2 | 6/2003 |
| EP | 1 384 445 A1 | 1/2004 |
| WO | WO 02/087437 A1 | 11/2002 |

OTHER PUBLICATIONS

International Search Report dated Mar. 30, 2006 for International Application No. PCT/US2005/041285.

* cited by examiner

*Primary Examiner*—Lee S Cohen
(74) *Attorney, Agent, or Firm*—CHristie, Parker & Hale, LLP

(57) ABSTRACT

A deflectable unilateral or bidirectional catheter for mapping and/or ablation, has a catheter body and a catheter tip section carrying a reference sensor and a scaffolding structure that is deployed for stabilizing and anchoring the catheter in or near the coronary sinus of the heart. In one embodiment, a control handle 16 at the proximal end of the catheter body 12 moves a sheath proximally to deploy the scaffolding structure. In a sheathless embodiment, the control handle moves a puller wire distally to deploy the scaffolding structure, which can be a generally spheroid shape, ovoid shape, basket shape, peanut shape and synaptic shape. The arrangement of the scaffolding structure, the reference sensor and a plurality of electrodes on the tip section can be varied as appropriate or needed.

17 Claims, 16 Drawing Sheets

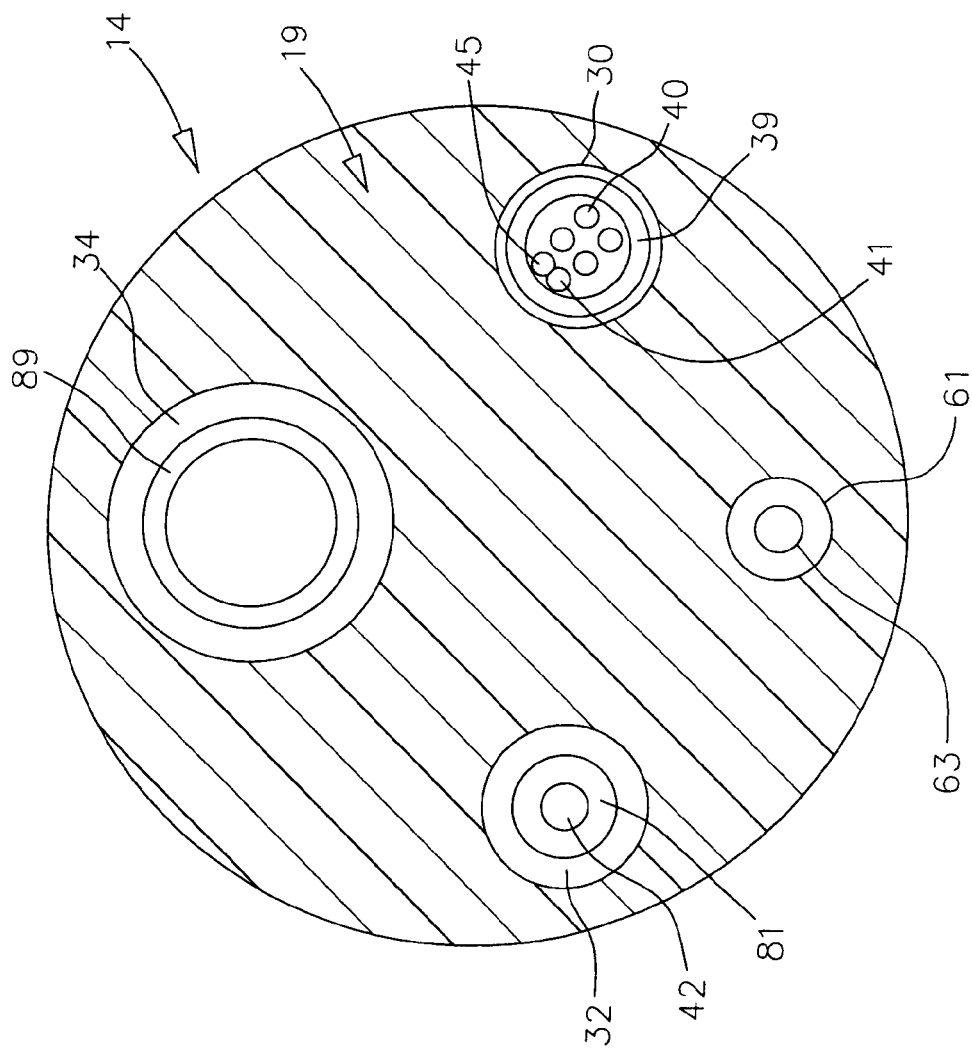

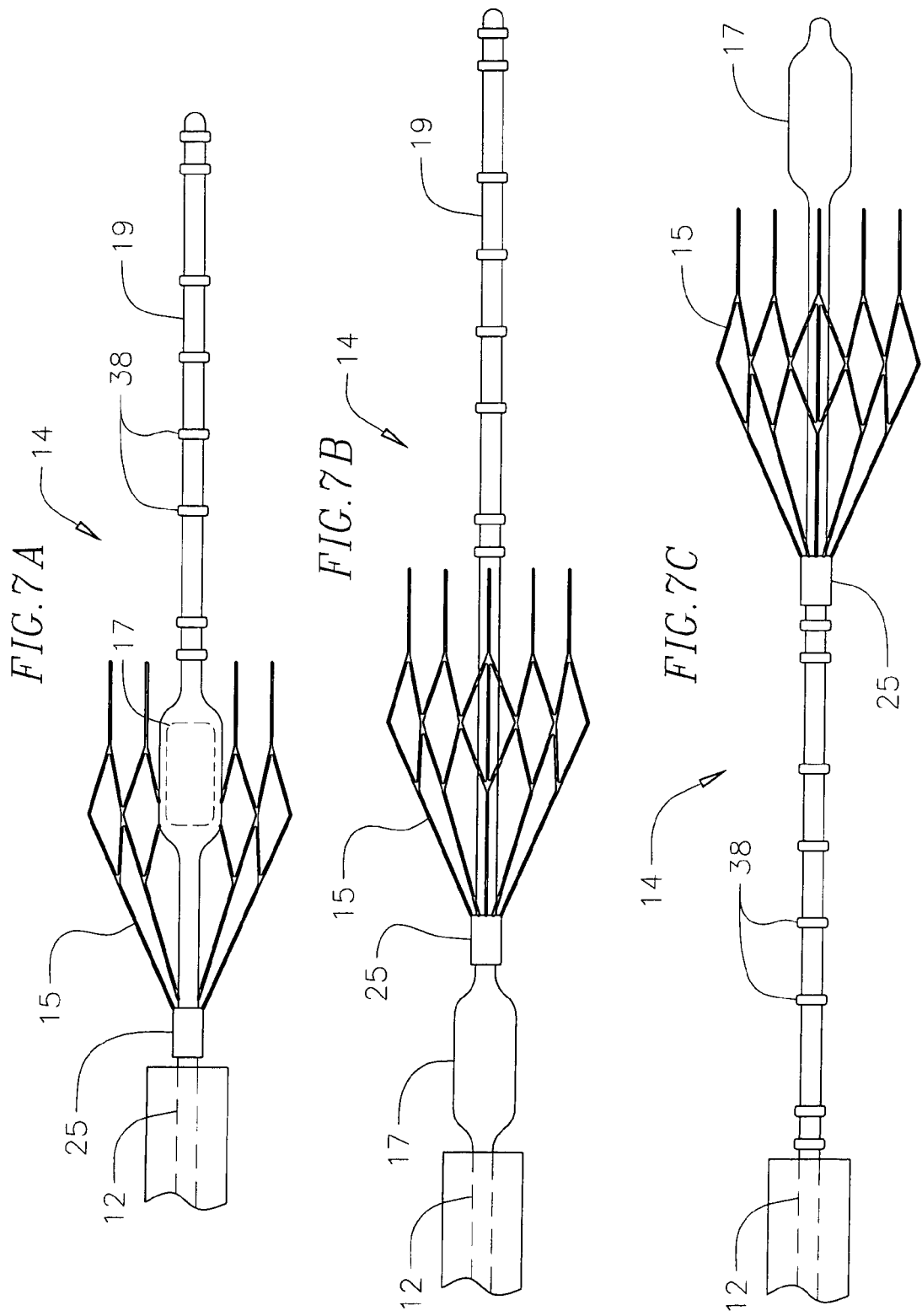

INTERNAL REFERENCE CORONARY SINUS CATHETER

FIELD OF INVENTION

The present invention relates generally to steerable catheters, and more specifically to steerable electrophysiology catheters for use in mapping of cardiac tissue.

BACKGROUND OF INVENTION

Atrial fibrillation is a common cardiac arrhythmia and a major cause of stroke. Atrial fibrillation results in a fast and irregular cardiac rhythm which often leads to palpitations and a deterioration of cardiac function with cardiac output decreasing by an average of 30%. There is also an increased incidence of intra cardiac thrombosis (blood clotting and coagulation) which can potentially lead to embolic events such as strokes. Consequently, 20 to 35% of cerebrovascular accidents (CVAs) are related to paroxysmal or chronic atrial fibrillation This condition is perpetuated by reentrant wavelets propagating in an abnormal atrial-tissue substrate. Various approaches, including electroanatomical and pulmonary vein isolation, have been developed to treat atrial fibrillation.

When the heart is viewed from the back, the most obvious structure lying in the coronary sulcus is the coronary sinus. This sinus receives most of the venous blood from the heart and empties the blood into the right atrium. Its tributaries are the small cardiac vein, the middle cardiac vein and the greater cardiac vein. Internal structures of the right atrium include the coronary sinus opening which may have small valve leaflets.

Difficulties in performing procedures within the coronary sinus include finding the ostium to the coronary sinus, preventing the catheter from slipping out of the coronary sinus and stabilizing the catheter in the coronary sinus in a beating heart. The catheter tends to slip out of the coronary sinus because of ante grade flow and movement of the heart and diaphragm. Moreover, the size and diameter of the coronary sinus can vary greatly between individuals and along the length of any one coronary sinus. Accordingly, significant disadvantages exist with current electrophysiological catheters ability to locate and work in the coronary sinus.

Where mapping of the heart is performed by means of electromagnetic sensing, the patient is placed in a magnetic field generated, for example, by situating under the patient a pad containing coils for generating a magnetic field. A reference electromagnetic sensor is fixed relative to the patient, e.g., taped to the patient's back, and a catheter containing a second electromagnetic sensor is advanced into the patient's heart. Each sensor comprises three small coils that in the magnetic field generate weak electrical signals indicative of their position in the magnetic field. Signals generated by both the fixed reference sensor and the second sensor in the heart are amplified and transmitted to a computer that analyzes the signals and then displays the signals on a monitor. By this method, the location of the sensor in the catheter relative to the reference sensor can be ascertained and visually displayed. Although the reference sensor is generally positioned outside the patient's body, it is also desirable for certain applications to position the reference sensor in the patient's heart, in particular, in or near the coronary sinus. Because the reference sensor serves as a reference location for the second electromagnetic sensor, movement of the reference sensor in or near the coronary sinus should preferably be minimized.

SUMMARY OF THE INVENTION

The present invention provides a deflectable unilateral or bidirectional catheter that is particularly useful in mapping and/or ablation procedures. The catheter comprises a control handle, a catheter body and a tip section that carries at least a reference sensor and a deployable scaffolding structure to stabilize the reference sensor and any other elements carried on the tip section in a tubular region of the heart, including the coronary sinus. The catheter body has a tubular wall, proximal and distal ends, and at least one lumen extending therethrough. The tip section comprises flexible tubing having proximal and distal ends and at least one lumen extending therethrough. The proximal end of the tip section is fixedly attached to the distal end of the catheter body. The reference sensor and a plurality of electrodes are carried on the flexible tubing of the tip section.

In one embodiment, the catheter includes an outer sheath that extends distally from the control handle, the length of the catheter body and the tip section until it reaches a distal end of the scaffolding structure such that the scaffolding structure is situated in the sheath in a collapsed configuration. To deploy the scaffolding structure, the control handle is configured to move the sheath proximally to expose the scaffolding structure and any proximal reference sensor and electrodes. The scaffolding structure made of a material that has shape memory, is relatively crush-resistant and readily self-expands to anchor and stabilize itself and adjacent reference sensor and electrodes within the tubular region against movement caused by blood flow and contractions of the heart muscle. Advantageously, the sheath is drawn proximally in a manner whereby the scaffolding structure remains generally stationary to avoid damaging the inner walls of the tubular region. Likewise, when the sheath is advanced distally to recapture and recover the scaffolding structure, the scaffolding structure remains generally stationary until it collapses and is surrounded circumferentially by the sheath.

In one embodiment, the tip section is configured such that the scaffolding structure is proximal of the reference sensor which is proximal of the electrodes. In other embodiments, the tip section is configured such that the scaffolding structure is distal of the sensor and/or the electrodes.

In an alternate embodiment, the catheter is without an outer sheath. While the sensor and the electrodes are mounted on the tubing of the tip section, the scaffolding structure rests in and is deployed from a lumen in the tip section. Distal movement of a puller wire or cable manipulated by the control handle advances the scaffolding structure beyond the distal end of the tip section and the scaffolding structure expands from its collapsed configuration into an expanded configuration to anchor and stabilize itself and the proximal reference sensor and electrodes carried on the tubing of the tip section. To recapture the scaffolding structure, the puller wire is moved proximally which draws the scaffolding structure proximally back into a generally surrounding circumferential relationship with the lumen of the tip section.

The scaffolding structure is constructed of a material with shape memory, e.g., nitinol, and may be a generally conical shape, a generally spherical shape, a generally ovoid shape, a basket shape, a peanut shape and a synaptic shape. Whereas the proximal end is generally a closed configuration, the distal end may be either a closed configuration or an open configuration. In one embodiment, the proximal end of the scaffolding structure is affixed to the tubing of the tip section. In another embodiment, the proximal end is affixed to the puller wire. Moreover, an anti-clotting coating, e.g., a bioactive heparin coating, may cover the scaffolding structure, the sheath and/or the catheter body.

The control handle is mounted at its distal end to the proximal end of the catheter body. The control handle comprises a housing having proximal and distal ends and a mechanism for deflecting the catheter tip section. In one embodiment, the control handle has another mechanism for moving the sheath distally and proximally. In another embodiment, the control handle has another mechanism for moving the scaffolding structure distally and proximally. In a further embodiment, the catheter body and tip section are configured with lumens and infusion tubes suitable for irrigation or dye applications. In yet another embodiment, the catheter body and tip section are configured with a lumen for front-loading of a guidewire which exits the catheter at a predetermined location along the length of the catheter body.

BRIEF DESCRIPTION OF THE DRAWINGS

These and other features and advantages of the present invention will be better understood by reference to the following detailed description when considered in conjunction with the accompanying drawings wherein:

FIG. 4A is a cross sectional view of the tip section of FIG. 3A.

DETAILED DESCRIPTION OF THE INVENTION

Figure 1:
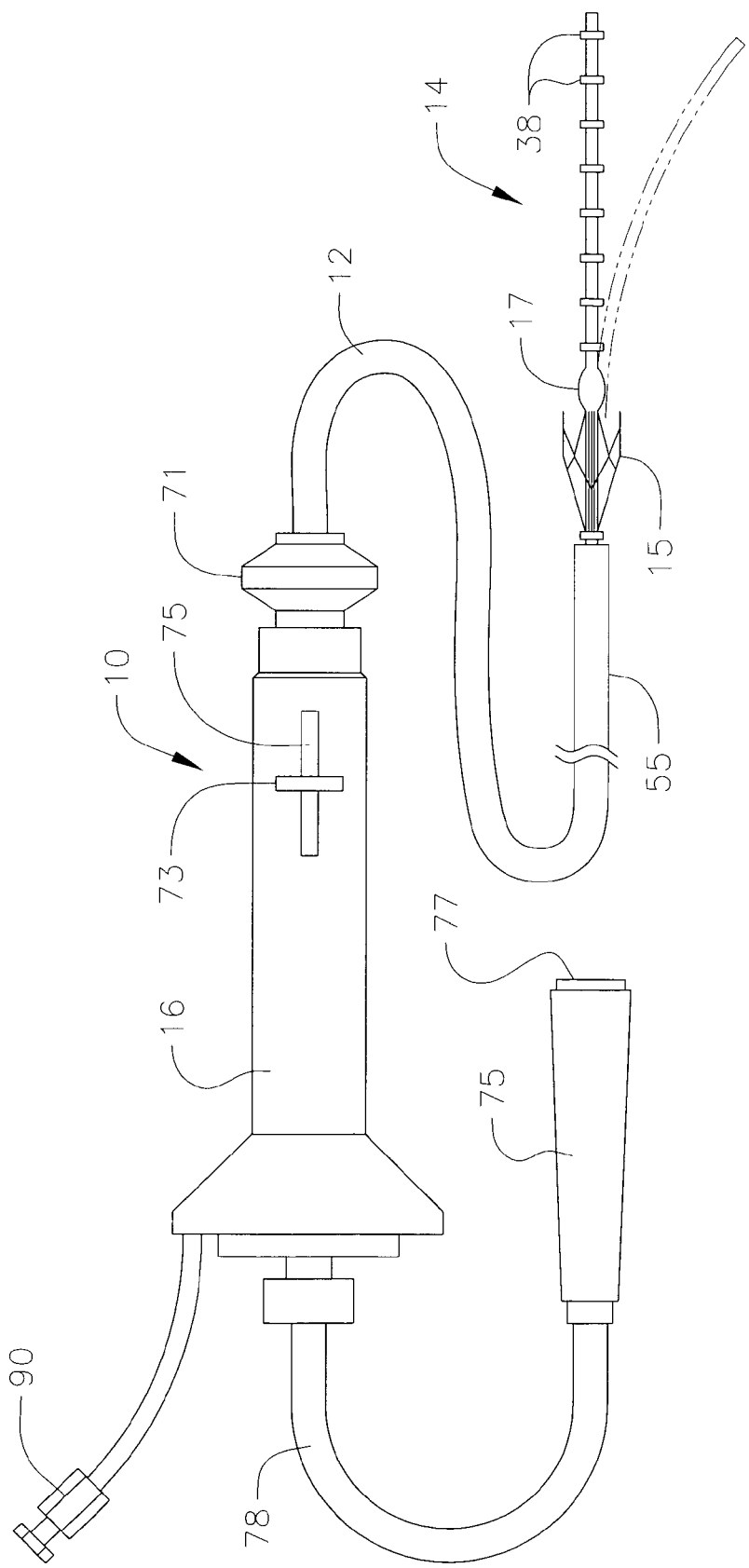
FIG. 1 is a side view of an embodiment of the catheter of the present invention.

In a preferred embodiment of the invention, there is provided a deflectable unilateral or bidirectional catheter having mapping and/or ablation electrodes, a reference sensor and a scaffolding structure that is deployed for stabilizing and anchoring the catheter in or near the coronary sinus of the heart. As shown in FIGS. 1-10, catheter 10 comprises an elongated catheter body 12 having proximal and distal ends, a tip section 14 at the distal end of the catheter body 12, and a control handle 16 at the proximal end of the catheter body 12. In accordance with a feature of the invention, the catheter tip section 14 includes an expandable scaffolding structure 15, a reference sensor 17 and a plurality of mapping electrodes 38.

Figure 2:
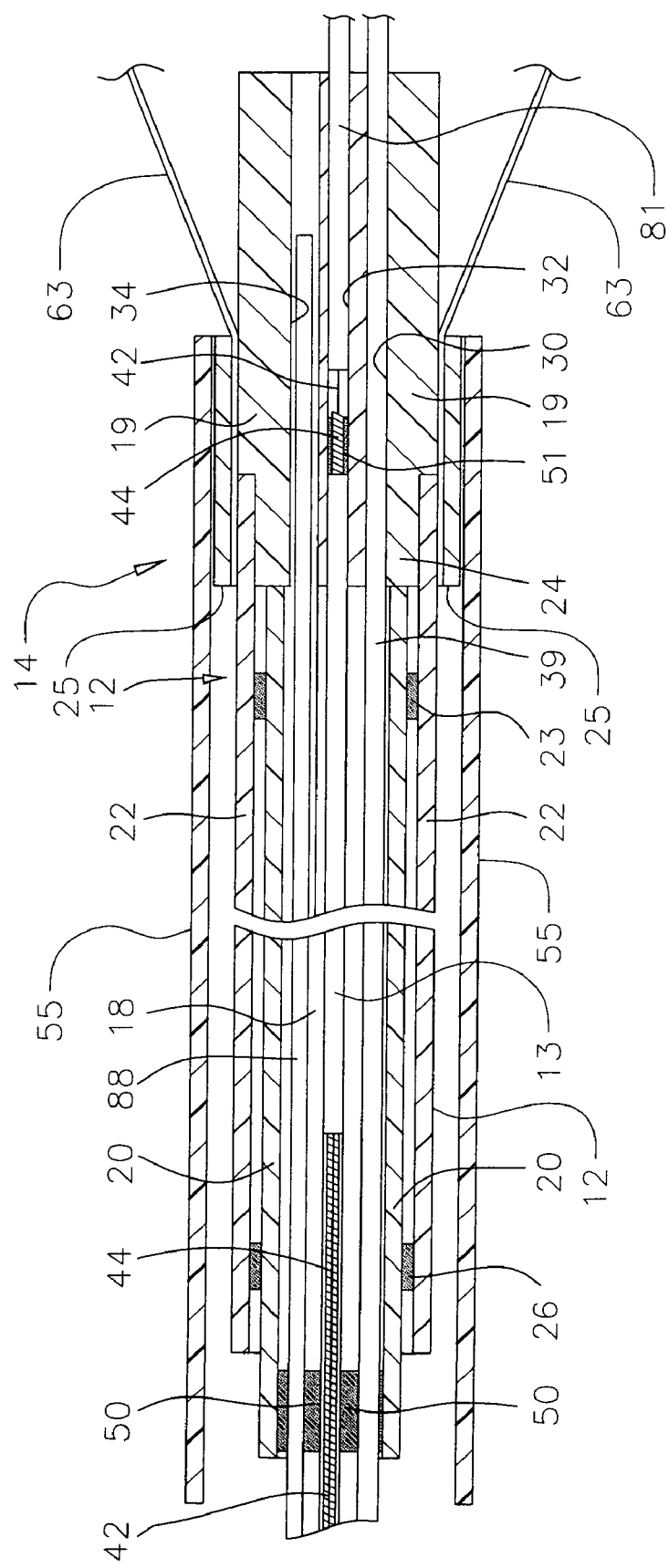
FIG. 2 is a side cross sectional view of a catheter body, including the junction between the catheter body and the tip section.

With reference to FIG. 2, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. One embodiment of the catheter body 12 may have a length ranging between about 100 cm and 120 cm, and preferably about 110 cm. Another embodiment of the catheter body 12 may have a length ranging between about 50 cm and 60 cm, and preferably about 55 cm. A presently preferred construction comprises an outer wall 22 made of a polyurethane, or PEBAX. The outer wall 22 comprises an imbedded braided mesh of stainless steel or the like to increase torsional stiffness of the catheter body 12 so that, when the control handle 16 is rotated, the tip section 14 of the catheter 10 will rotate in a corresponding manner.

Extending through the single lumen 18 of the catheter body 12 are lead wires and a compression coil through which a puller wire extends. A single lumen catheter body may be preferred over a multi-lumen body because it has been found that the single lumen body permits better tip control when rotating the catheter. The single lumen permits the lead wires and the puller wire surrounded by the compression coil to float freely within the catheter body. If such wires and tube were restricted within multiple lumens, they tend to build up energy when the handle is rotated, resulting in the catheter body having a tendency to rotate back if, for example, the handle is released, or if bent around a curve, to flip over, either of which are undesirable performance characteristics.

The outer diameter of the catheter body 12 is not critical, but is preferably no more than about 8 french, preferably about 7 french and more preferably about 6 french. Likewise the thickness of the outer wall 22 is not critical, but is thin enough so that the central lumen 18 can accommodate at least a puller wire and lead wires. If appropriate, the lumen 18 can be sized to also accomodate any other wires, cables or tubes. The inner surface of the outer wall 22 is lined with a stiffening tube 20, which can be made of any suitable material, such as polyimide or nylon. The stiffening tube 20, along with the braided outer wall 22, provides improved torsional stability while at the same time minimizing the wall thickness of the catheter, thus maximizing the diameter of the central lumen 18. The outer diameter of the stiffening tube 20 is about the same as or slightly smaller than the inner diameter of the outer wall 22. Polyimide tubing is presently preferred for the stiffening tube 20 because it may be very thin walled while still providing very good stiffness. This maximizes the diameter of the central lumen 18 without sacrificing strength and stiffness.

A particularly preferred catheter has an outer wall 22 with an outer diameter of from about 0.10 inch to about 0.094 inch and an inner diameter of from about 0.061 inch to about 0.065 inch and a polyimide stiffening tube 20 having an outer diameter of from about 0.060 inch to about 0.064 inch and an inner diameter of from about 0.051 inch to about 0.056 inch.

Figure 3:
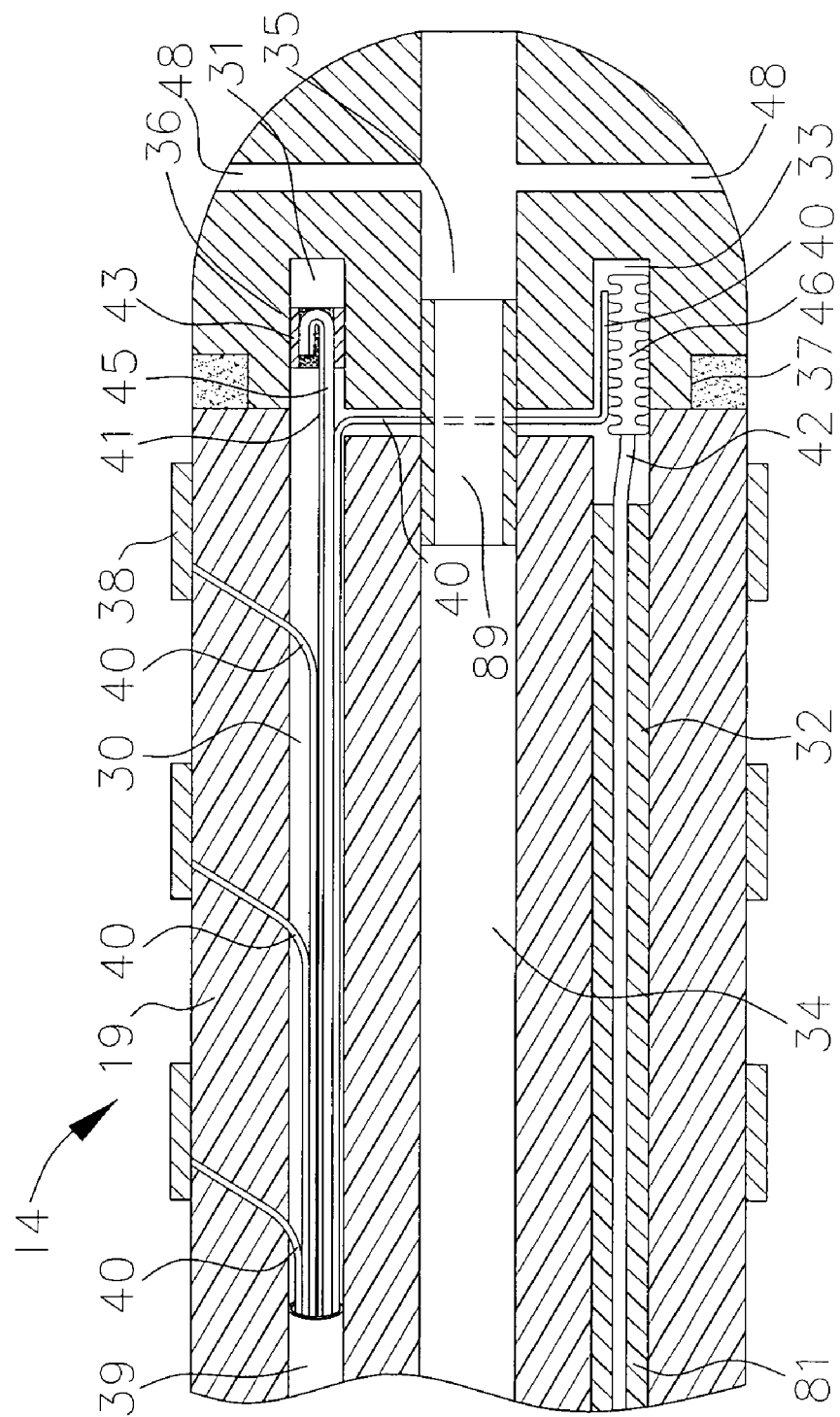
FIG. 3 is a side cross sectional view of an embodiment of the distal end of the tip section.
Figure 4:
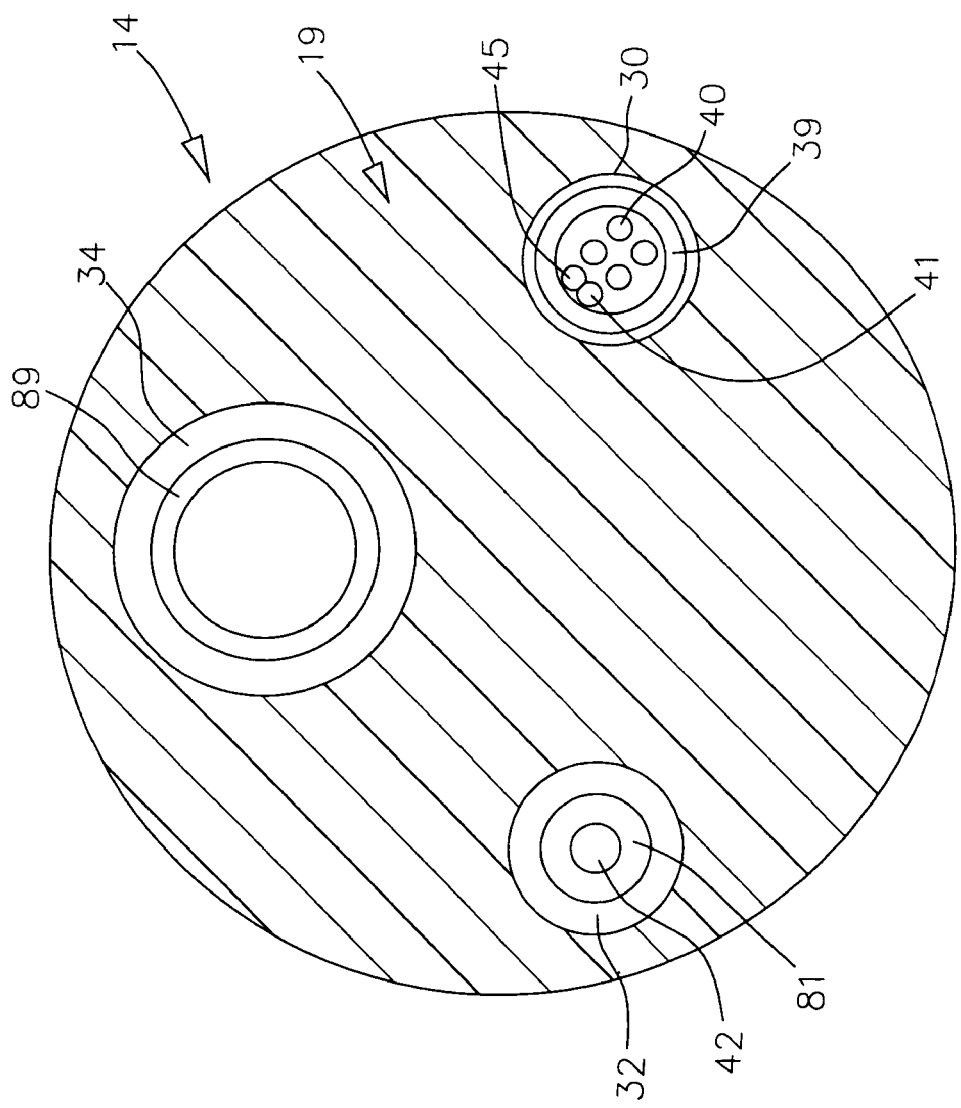
FIG. 4 is a cross sectional view of the tip section of FIG. 3.

As shown in FIGS. 3 and 4, the tip section 14 comprises a short section of tubing 19 having at least two lumens. The tip section 14 has a length ranging between about 4.0 cm and 10 cm, preferably about 6.0 and 7.0 and more preferably about 6.5 cm. The tubing 19 is made of a suitable non-toxic material that is preferably more flexible than the catheter body 12. A presently preferred material for the tubing 19 is braided polyurethane, i.e., polyurethane with an embedded mesh of braided stainless steel or the like. The outer diameter of the tip section 14, like that of the catheter body 12, is preferably no greater than about 6 french and more preferably 5 french. The size of the lumens is not critical. In a particularly preferred embodiment, the first lumen 30 and second lumen 32 are generally about the same size, each having a diameter of from about 0.019 inch to about 0.025 inch, preferably 0.022 inch. There may also be a third lumen 34 having a slightly larger diameter of from about 0.032 inch to about 0.040 inch, preferably 0.038 inch.

A preferred means for attaching the catheter body 12 to the tip section 14 is illustrated in FIG. 2. The proximal end of the tip section 14 comprises an outer circumferential notch 24 that receives the inner surface of the outer wall 22 of the catheter body 12. The tip section 14 and catheter body 12 are attached by glue or the like. Before the tip section 14 and catheter body 12 are attached, however, the stiffening tube 20 is inserted into the catheter body 12. The distal end of the stiffening tube 20 is fixedly attached near the distal end of the catheter body 12 by forming a glue joint 23 with polyurethane glue or the like. Preferably a small distance, e.g., about 3 mm, is provided between the distal end of the catheter body 12 and the distal end of the stiffening tube 20 to permit room for the catheter body 12 to receive the notch 24 of the tip section 14. A force is applied to the proximal end of the stiffening tube 20, and, while the stiffening tube 20 is under compression, a first glue joint (not shown) is made between the stiffening tube 20 and the outer wall 22 by a fast drying glue, e.g. Super Glue®. Thereafter a second glue joint 26 is formed between the proximal ends of the stiffening tube 20 and outer wall 22 using a slower drying but stronger glue, e.g., polyurethane.

If desired, a spacer can be located within the catheter body between the distal end of the stiffening tube and the proximal end of the tip section. The spacer provides a transition in flexibility at the junction of the catheter body and tip section, which allows this junction to bend smoothly without folding or kinking. A catheter having such a spacer is described in U.S. Pat. No. 5,964,757, entitled "Steerable Direct Myocardial Revascularization Catheter", the disclosure of which is incorporated herein by reference.

As illustrated in FIG. 3, at the distal end of the tip section 14 is a tip end or dome 36 with an atraumatic distal end. Preferably the dome 36 has a diameter about the same as the outer diameter of the tubing 19. The dome 36 is generally solid, having a fluid passage 35 and a pair of blind holes 31 and 33 that correspond in size and location to the three lumens 34, 30 and 32 respectively in the tip section 14. The blind holes 31 and 33 extend from the proximal end of the dome 36, but do not extend through to the distal end of the dome. In the embodiment shown, the fluid passage 35 comprises an axial branch that is in axial alignment with the third lumen 34 and six transverse branches 48 that extend radially from the distal end of the axial branch to the outer surface of the dome 36. It is understood that the configuration of the fluid passage may vary as desired.

A preferred dome has an effective length, i.e., from its distal end to the distal end of the tubing, of about 3.5 mm, and an actual length, i.e., from its distal end to its proximal end, of about 4.0 mm. As shown in FIG. 3, the dome 36 is attached to the tubing 19 by creating a notch 37 in the proximal end of the dome 36, placing the proximal end of the dome on the distal end of the tubing 19, and filling the notch 37 with glue. The wires and tubes that extend into the dome 36 help to keep the dome in place on the tip section.

The dome 36 and the ring electrodes 38 can be made of any suitable material, and are preferably machined from platinum-iridium bar (90% platinum/10% iridium). The ring electrodes 38 are each connected to a separate lead wire 40. The lead wires 40 extend through the first lumen 30 of tip section 14, the central lumen 18 of the catheter body 12, and the control handle 16, and terminate at their proximal end in an input jack (not shown) that may be plugged into an appropriate monitor (not shown). The portion of the lead wires 40 extending through the central lumen 18 of the catheter body 12, control handle 16 and proximal end of the tip section 14 are enclosed within a protective nonconductive sheath 39, which can be made of any suitable material, preferably polyimide. The protective sheath 39 is anchored at its distal end to the proximal end of the tip section 14 by gluing it in the second lumen 32 with polyurethane glue or the like.

The lead wires 40 are attached to ring electrodes 38 by any conventional technique. Where the dome 36 is a tip electrode, connection of a lead wire 40 to the tip electrode is accomplished, for example, by welding the lead wire 40 into the second hole 33 in the tip electrode.

Connection of a lead wire 40 to a ring electrode 38 is preferably accomplished by first making a small hole through the tubing 19. Such a hole can be created, for example, by inserting a needle through the tubing 19 and heating the needle sufficiently to form a permanent hole. A lead wire 40 is then drawn through the hole by using a microhook or the like. The ends of the lead wire 40 are then stripped of any coating and soldered or welded to the underside of the ring electrode 38, which is then slid into position over the hole and fixed in place with polyurethane glue or the like.

A temperature sensing means may be provided for the tip electrode 36 and, if desired, the ring electrodes 38. Any conventional temperature sensing means, e.g., a thermocouple or thermistor, may be used. With reference to FIG. 3, a preferred temperature sensing means for the tip electrode 36 comprises a thermocouple formed by a wire pair. One wire of the wire pair is a copper wire 41, e.g., a number "40" copper wire. The other wire of the wire pair is a constantan wire 45, which gives support and strength to the wire pair. The wires 41 and 45 of the wire pair are electrically isolated from each other except at their distal ends where they contact and are twisted together, covered with a short piece of plastic tubing 43, e.g., polyimide, and covered with epoxy. The plastic tubing 43 is then attached in the first blind hole 31 of the tip electrode 36, by polyurethane glue or the like. The wires 41 and 45 extend through the first lumen 31 in the tip section 14. Within the catheter body 12 the wires 41 and 45 extend through the protective sheath 39 with the lead wires 40. The wires 41 and 45 then extend out through the control handle 16 and to a connector (not shown) connectable to a temperature monitor (not shown).

Alternatively, the temperature sensing means may be a thermistor. A suitable thermistor for use in the present invention is Model No. AB6N2-GC14KA143E/37C sold by Thermometrics (New Jersey).

Referring to FIGS. 2 and 3, a puller wire 42 extends through the catheter body 12, is anchored at its proximal end to the control handle 16, and is anchored at its distal end to the tip section 14. The puller wire 42 is made of any suitable metal, such as stainless steel or Nitinol, and is preferably coated with Teflon® or the like. The coating imparts lubricity to the puller wire 42. The puller wire 42 preferably has a diameter ranging from about 0.006 to about 0.010 inches.

A compression coil 44 is situated within the catheter body 12 in surrounding relation to the puller wire 42. The compression coil 44 extends from the proximal end of the catheter body 12 to the proximal end of the tip section 14. The compression coil 44 is made of any suitable metal, preferably stainless steel. The compression coil 44 is tightly wound on itself to provide flexibility, i.e., bending, but to resist compression. The inner diameter of the compression coil 44 is preferably slightly larger than the diameter of the puller wire 42. The Teflon.RTM. coating on the puller wire 42 allows it to slide freely within the compression coil 44. If desired, particularly if the lead wires 40 are not enclosed by a protective sheath 39, the outer surface of the compression coil 44 can be covered by a flexible, non-conductive sheath 13, e.g., made of polyimide tubing, to prevent contact between the compression coil 44 and any other wires within the catheter body 12.

The compression coil 44 is anchored at its proximal end to the proximal end of the stiffening tube 20 in the catheter body 12 by glue joint 50 and at its distal end to the tip section 14 by glue joint 51. Both glue joints 50 and 51 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 22 of the catheter body 12 and the stiffening tube 20 which is heated sufficiently to form a permanent hole. The glue is then introduced through the hole to the outer surface of the compression coil 44 and wicks around the outer circumference to form a glue joint about the entire circumference of the compression coil 44.

The puller wire 42 extends into the second lumen 32 of the tip section 14. The puller wire 42 is anchored at its distal end to the tip electrode 36 within the second blind hole 33. A preferred method for anchoring the puller wire 42 within the tip electrode 36 is by crimping metal tubing 46 to the distal end of the puller wire 42 and soldering the metal tubing 46 inside the second blind hole 33. Anchoring the puller wire 42 within the tip electrode 36 provides additional support, reducing the likelihood that the dome/tip electrode 36 will fall off the tip section 14. Alternatively, the puller wire 42 can be attached to the side of the tip section 14. Within the second lumen 32 of the tip section 14, the puller wire 42 extends through a plastic, preferably Teflon®, sheath 81, which prevents the puller wire 42 from cutting into the wall of the tip section 14 when the tip section is deflected.

Figure 5A:
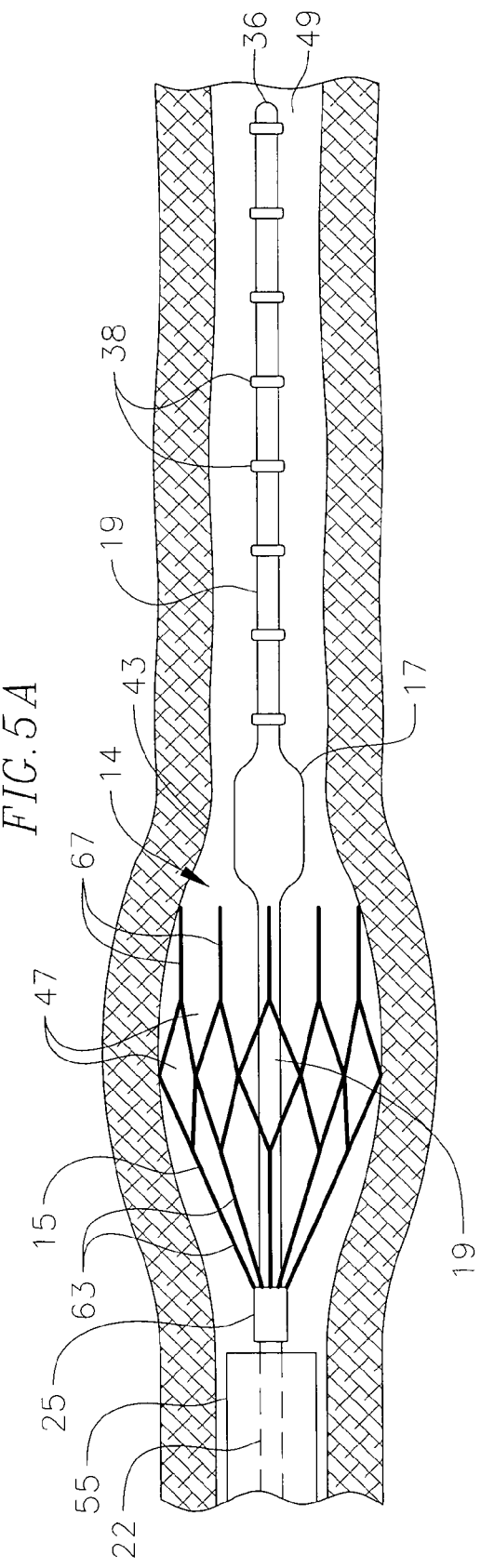
FIG. 5A is a side view of an embodiment of the tip section deployed within a tubular region of or near the heart.
Figure 5B:
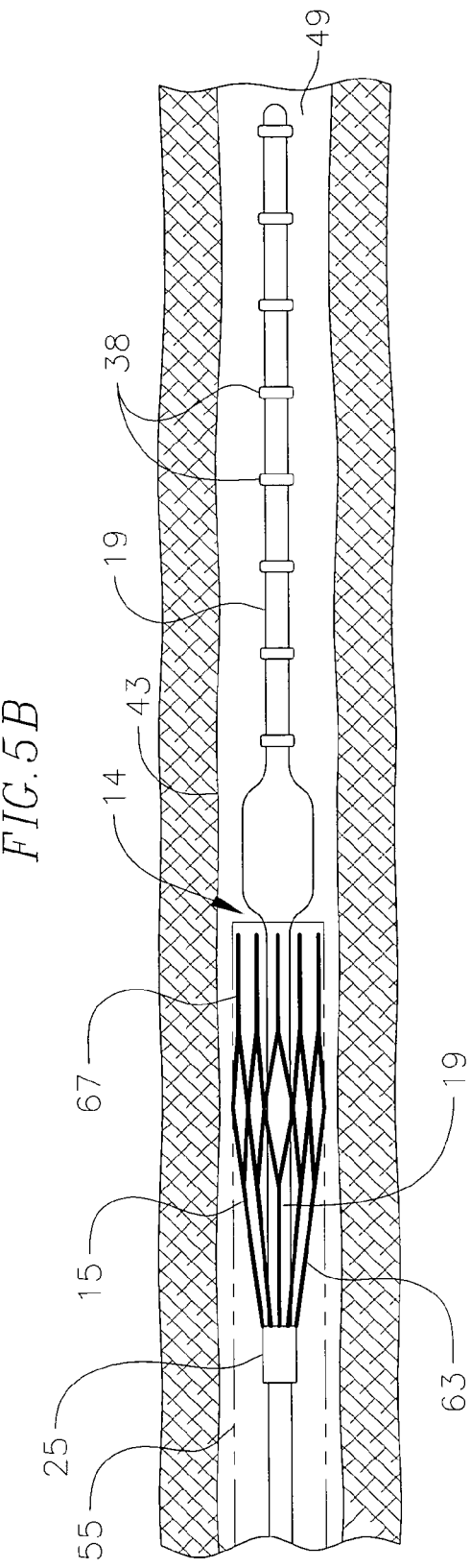
FIG. 5B is a side view of the tip section of FIG. 5A recaptured in the sheath.

In the embodiment shown in FIGS. 5A and 5B, there are eight ring electrodes 38 mounted on the tip section 14 proximal to dome 36. It is understood that the presence, number and positioning of the ring electrodes 38 may vary as desired. For example, the tip section 14 may carry any number of electrodes ranging between about four and 20, and more preferably between eight and ten for an octapolar or a decapolar catheter. Each ring electrode 38 is slid over the tubing 19 and fixed in place by glue or the like. In the illustrated embodiments of FIGS. 7A-7E, the two most distal ring electrodes are separated by a distance of about 2.0 mm from each other, from middle to middle of the electrodes, and the two most proximal ring electrodes are separated by a distance of about 2.0 mm from each other, from middle to middle of the electrodes. In between these two most distal and two most proximal electrodes, the electrodes are separated by a distance of about 5.0 mm, from middle to middle of the electrodes. The electrodes therefore assume a 2-5-2 configuration in the illustrated embodiments. As such, the eight ring electrodes span a distance ranging between 2.0 cm and 5.0 cm, and preferably about 2.9 cm, with each ring electrode being about 1.5 mm wide. As understood by one of ordinary skill in the art, other configurations and distance spans are possible.

Figure 7D:
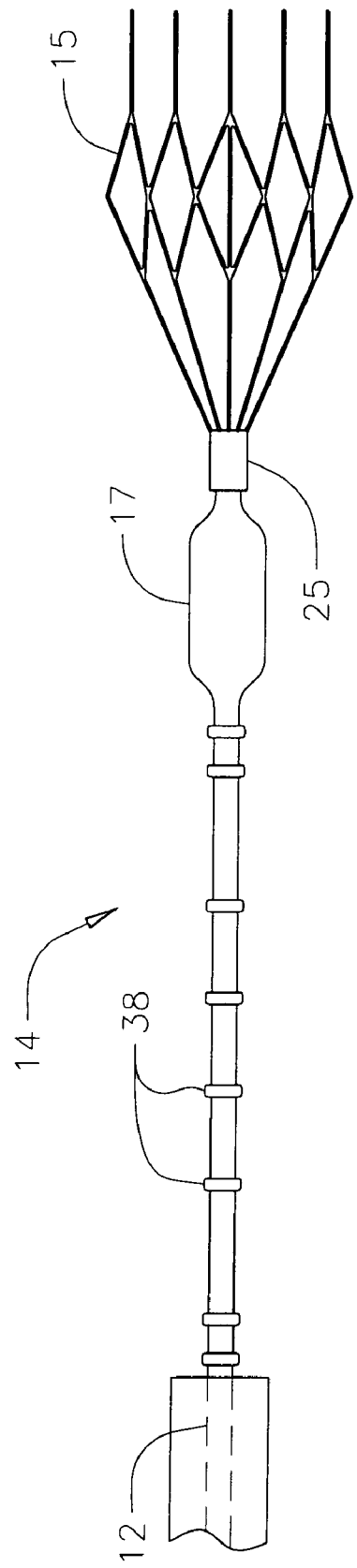
FIGS. 7A-7C are side views of other embodiments of the tip section.
Figure 7E:
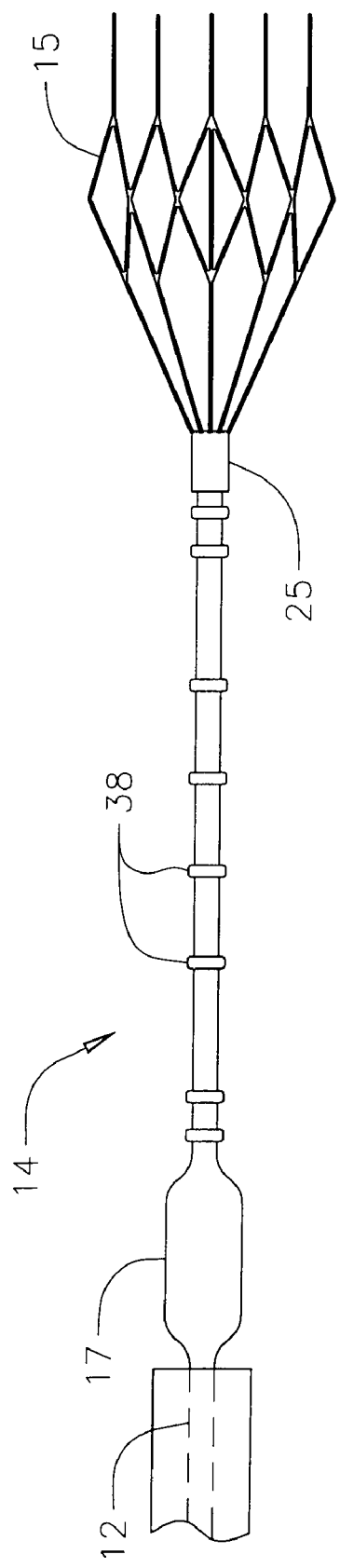
Figure 8A:
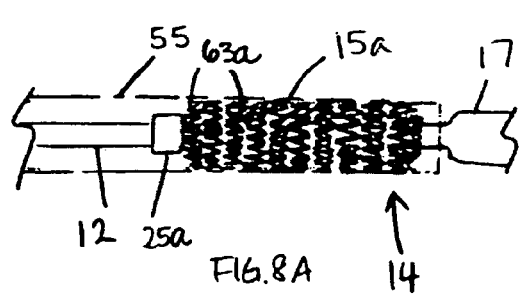
FIGS. 8A, 8B, 9A, 9B, 10A, 11, 16A 16B, 17A and 17B are side views of other embodiments of the scaffolding structure, shown in the recaptured configuration and the deployed configuration.
Figure 8B:
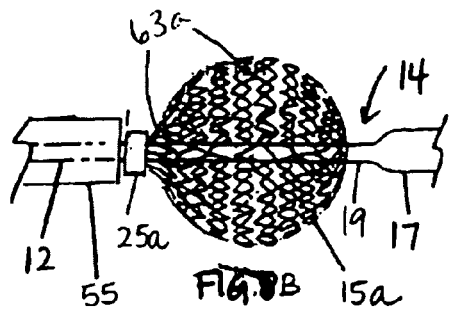
Figure 9A:
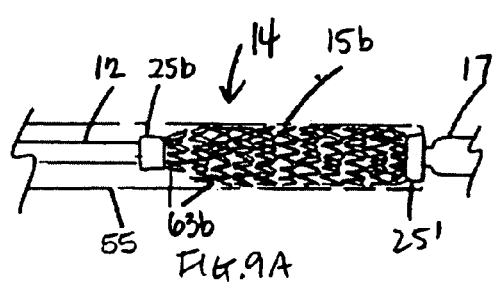
Figure 9B:
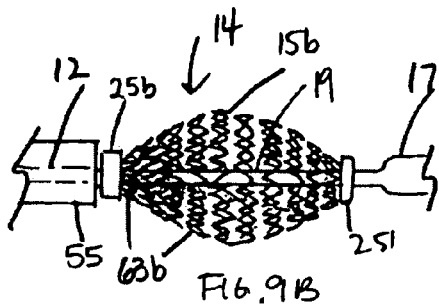

The most distal electrode is separated from its nearest distal tip element, if any, by a distance of at least 1.0 mm. The most proximal electrode is separated from its nearest proximal tip element, if any, by a distance of at least 1.0 mm. As shown in FIGS. 5A, 7A and 7E, the nearest proximal element is the scaffolding structure or the sensor. As shown in FIGS. 7c, 7D and 7E, the nearest distal element is the scaffolding structure or the sensor.

As also illustrated in FIGS. 5A and 5B, affixed to the catheter tip section 14 is the scaffolding structure 15 which is collapsible to assume a collapsed configuration (FIG. 5B) while the catheter body 12 and the tip section 14 are advanced to the target site and is self-expandable upon deployment at the target site to assume an expanded configuration (FIG. 5A). The expanded configuration enables the scaffolding structure to contact, conform to and/or brace against the inner walls 43 of a tubular region 49 of the heart, for example, the coronary sinus. As such, the scaffolding structure stabilizes the catheter tip section 14, including in particular the reference sensor 15, in the tubular region against movement due to blood flow, the heart beating and the pull on the heart by the diaphragm. The scaffolding structure 15 has distal and proximal ends and a F length ranging between about 1.0 cm to 2.2 cm, preferably about 1.2 cm to 2.5 cm, and more preferably about 2.0 cm. The scaffolding structure 15 may be of any suitable construction, for example, with a piece or pieces of wire that are bent into a number of turns, or a wire mesh that is rolled into a generally tubular shape. The scaffolding structure may also be made with a flat metal sheet with a number of openings formed in rows therein (e.g., by laser and temperature-effected expansion), or with a piece of metal cannula with a number of openings formed in the circumference thereof. There may be open cells and/or closed cells 47, loops and/or struts, and interconnections or intersections forming zig-zag, serpentine and/or sawtooth patterns. In any case, the scaffolding structure 15 is described generally herein as having wire or spine formations spanning its length and/or width regardless of the method of manufacture.

The scaffolding structure 15 may be made of any suitable material that has shape-memory, for example, nitinol, such that the structure readily collapses into a generally linear profile when compressed and expands radially under shape-memory into a generally nonlinear profile. In the illustrated embodiment of FIGS. 1, 2, 5A and 5B, the scaffolding structure 15 has a generally conical configuration, with a closed proximal end and an open distal end. As shown in FIG. 2, proximally-extending spines or wires 23 of the scaffolding structure 15 forming the closed proximal end are affixed to the proximal end of the tubing 19 of the catheter tip section 14 by a short tubular section 25. In a preferred embodiment, the proximally-extending spines 63 are soldered or otherwise affixed to the short tubular section 25 which is then slid onto the tubing 19 when stretched or otherwise elongated longitudinally under an external force to reduce its circumference. The circumference of the short tubular section 25 is sized such that it fits snugly on the tubing 19 and is securely fastened to the catheter tip section 14 when the tubing is released from the external force.

As further shown in FIGS. 5A and 5B, distally-extending spines or wires 67 of the scaffolding structure 15 forming its distal end are generally parallel to and arranged in a generally circumferential relationship with the tubing 19. Between the closed proximal end and the open distal end are open and closed cells 47 formed from any variety of patterns, including zig-zag, serpentine and/or sawtooth. These cells expand circumferentially when the scaffolding 15 is deployed and contract circumferentially when the scaffolding 15 is collapsed. The number of distally-extending spines 67 generally equals the number of proximally-extending spines 63, which number ranges between two and four spines, and preferably three spines. The scaffolding structure 15 has an expanded width or diameter ranging about 0.5 cm to 3.0 cm, and preferably about 2.0 cm. When collapsed the scaffolding structure 15 fits within the sheath 55 which is described below in further detail.

Figure 6:
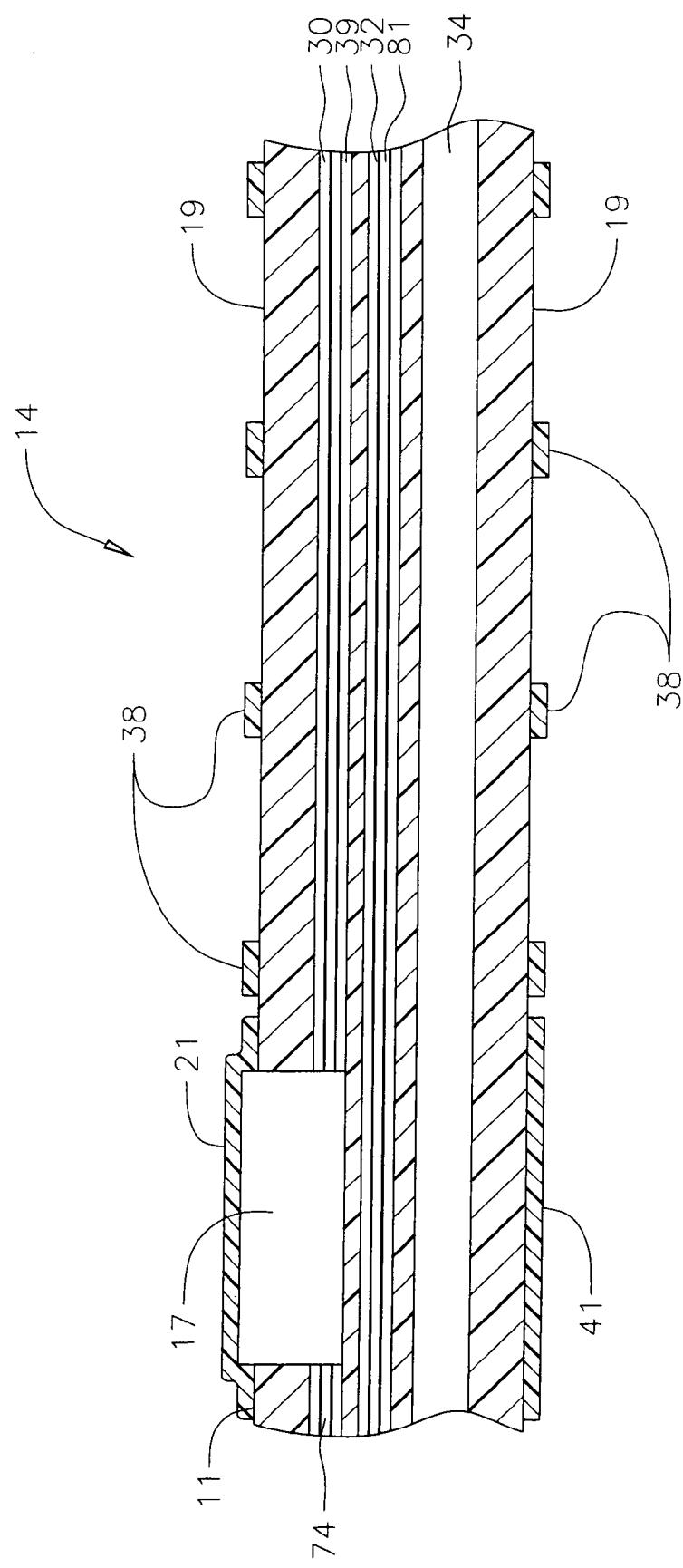
FIG. 6 is a side cross sectional view of an embodiment of the tip section having the sensor.

In accordance with a feature of the present invention, the electromagnetic reference sensor 17 is also carried on the tip section 14. The sensor 17 has a length L ranging between about 1.0 mm and 1.5 mm and preferably about 1.2 mm. As shown in FIG. 6, the reference sensor sits in a notch 11 configured in the tubing 19 and is affixed by glue or any appropriate adhesive. Covering the sensor is a short tubing 21 of biocompatible material, for example, Pellathane. A reference electromagnetic sensor suitable for the present invention is available from Biosense Webster, Inc., Irwindale, Calif.

In the disclosed embodiment of FIGS. 5A and 5B, the scaffolding structure 15 is distal of the distal end of the catheter body 12 and proximal of the reference sensor 17 which is proximal of the ring electrodes 38. In particular, the sensor 17 may be distal of the open distal end of the scaffolding structure (FIGS. 5a and 5B) or merely distal of the closed proximal end of the scaffolding structure such that the sensor sits within and is overlapped by the scaffolding structure (FIG. 7A). In another embodiment of the present invention, the sensor 17 may be proximal of the scaffolding structure 15 (FIG. 7B). For these embodiments, it is understood by one of ordinary skill in the art that it may be preferable to position the sensor 17 and the scaffolding structure 15 adjacent or in overlapping arrangement in varying degrees with each other on the catheter tip section 14 so that the sensor receives a greater if not maximum benefit of the stabilization effects of the scaffolding structure. However, there may also be instances where it may be preferable to position the ring electrodes 38 between the sensor 17 and the scaffolding structure 15 (FIG. 7E). In yet another embodiment, the ring electrodes may also be proximal of both the sensor 17 and the scaffolding structure 15 (FIGS. 7C and 7D).

In accordance with the present invention, a protective sheath 55 extends along the length of the catheter body 12 from within the control handle 16 to the catheter tip section 14, and more particular, to the distal end of the scaffolding structure 15. The sheath 55 is movable distally and proximally along the longitudinal axis of the catheter body and tip section by means of the control handle. As shown in FIG. 5B, the sheath 55 (in broken lines) is sufficiently long in length to cover the scaffolding structure 15 in its entirety. The sheath 55 is manipulated by the control handle 16 to move proximally for deploying the scaffolding structure once the catheter tip section 14 reaches the target site, for example, a tubular region such as the coronary sinus. Therefore, the scaffolding structure 15 is safely housed in the sheath 55 during advancement of the catheter body 12 and tip section 14 in the patient's body. In particular, the catheter control handle 16 is configured to draw the sheath 55 proximally while leaving the scaffolding structure 15 generally stationary during deployment at the target site. As such, the catheter 10 minimizes, if not altogether avoids, any risk of the inner wall 43 tearing due to abrasion with the scaffolding structure during deployment.

Because the sheath 55, the sensor 17 and the ring electrodes 38 need to be exposed at the target site, the sheath 55 extending to the distal end of the scaffolding structure before deployment is drawn proximally such that all of these elements on the tip section 14 are exposed. To that end, it is understood that for the various embodiments possible including those illustrated in FIGS. 5A-7E, the distance by which the sheath 55 is drawn proximally varies depending on the relative positioning of the scaffolding structure 15, the sensor 17 and the ring electrodes 38. For example, where the scaffolding structure 15 is the most proximal element on the tip section 14 (FIG. 7A), the sheath need only expose the scaffolding structure, that is, be drawn proximally a distance equaling generally the length of the scaffolding structure 15. However, where the scaffolding structure 15 is the most distal element on the tip section 14 (FIGS. 7D and 7E), the sheath needs to expose all three elements, that is, be drawn a distance equaling generally the combined lengths of the tubing 19 and the scaffolding structure 15. Where the scaffolding structure 15 is between the electrodes 38 and the sensor 17 (FIGS. 7B and 7C), the sheath need only to expose the scaffolding structure and the proximal element, that is, be drawn a distance equaling generally the length between the proximal end of the tip section 14 and the distal end of the scaffolding structure 15. Thus, depending on the arrangement and order of the scaffolding structure, the sensor 17 and the ring electrodes 38 on the catheter tip section 14, so varies the distance by which the catheter control handle 16 draws the sheath 55 proximally so as to expose at least the scaffolding structure 15 and any proximal sensor and ring electrodes. In accordance with a feature of the present invention, it is the sheath 55 which is drawn proximally or advanced distally by the control handle 16 while the scaffolding structure 15 generally remains stationary during deployment and recapture.

Because the scaffolding structure 15 is constructed of a pliable material with shape memory, it freely expands into the expanded configuration when the sheath 55 is moved proximally. Upon expansion, the scaffolding structure contacts and anchor itself against the inner wall 43 of the tubular region 49 (FIG. 5A). When the sheath 55 (shown in broken lines in FIG. 5B) is moved distally, the scaffolding structure 15 readily collapses into a collapsed and compact configuration such that it is recovered and housed entirely in the sheath 55. In that regard, the diameter of the sheath 55 is sized to accommodate longitudinal movement along the catheter body 12, the tip section 14, the scaffolding structure and any proximal sensor and ring electrodes. Accordingly, the diameter of the sheath 55 ranges between about 6 and 9 french, and preferably about 7 french with an inner diameter ranging between about 0.090 inches to about 0.130 inches, and more preferably about 0.110 inches.

Figure 10A:
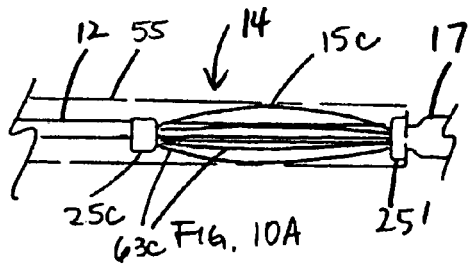
Figure 11:
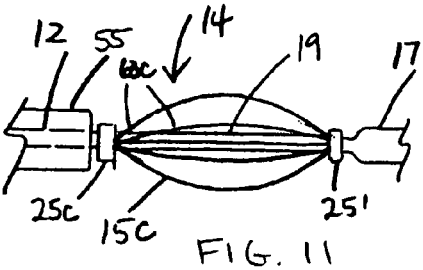
Figure 16A:
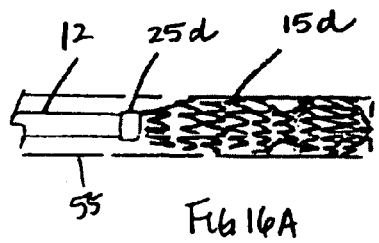
Figure 16B:
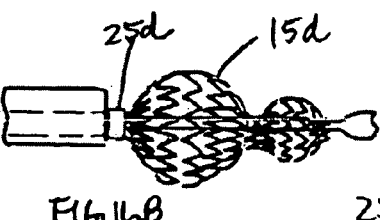
Figure 17A:
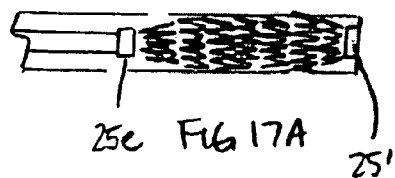
Figure 17B:
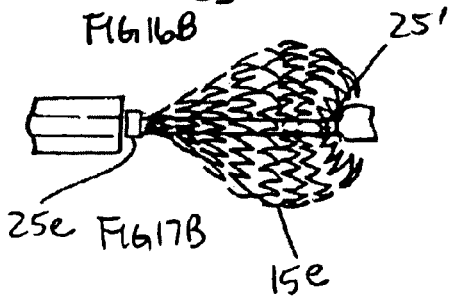

The scaffolding structure 15 can assume other configurations, including a generally spherical shape 15a (shown collapsed in FIG. 8A and expanded in FIG. 8B), a generally ovoid shape 15b (shown collapsed in FIG. 9A and expanded in FIG. 9B) and a basket shape 15c (shown collapsed in FIG. 10A and expanded in FIG. 11). There are also a peanut shape 15d (shown collapsed in FIG. 16A and expanded in FIG. 16B) with a larger proximal generally spheroid portion connected to a small distal generally spheroid portion, and a synaptic shape 15e (shown collapsed in FIG. 17A and expanded in FIG. 17B). The distal end of the synaptic shape 15e expands radially and distally upon expansion to generally envelop at least the proximal end of the sensor such that the sensor sits in a generally centered dimple, or in an elongated depression or valley at the distal end of the shape 15e.

The spherical shape structure 15a has a closed distal end and a closed proximal end. The proximal end is fixedly mounted on the tubing 19 of the tip section 14 by means of a proximal ring 25a in a similar manner as described for the conical shape structure (see FIG. 2). Similarly for the ovoid, basket, peanut and synaptic structures 15b-15e, proximal rings 25b-25e, respectively, are provided and fixedly mounted on the tubing 19. The distal ends of these structures (each of which may or may not have a distal ring 25' to which distally extending spines 67 are affixed to) however are free to slide along the tubing 19 so as to allow the structures to lengthen and shorten along the tubing 19 as needed to absorb movement of the tubular region as a result of the heart beating and also to enable expansion and contraction of the scaffolding structure itself during deployment and recapture.

Each of the structures 15a-15e has an expanded diameter ranging between about 0.5 cm and 3.0 cm and more preferably is about 2.0 cm. Each of the structures has a length ranging between 1.0 cm and 3.0 cm and more preferably is about 2.0 cm. Moreover, the basket structure 15c has a plurality of spines that may number between four and ten, and more preferably between six and eight. Other suitable shapes and structures that may be adopted by the scaffolding structures may be described in U.S. Pat. Nos. [provided by Minh Dinh] 6,771,996, 6,758,830, 678-183 and/or 6,699,064, the entire disclosures of which are incorporated herein by reference.

An infusion tube is provided within the catheter body 12 for infusing fluids, e.g., heparin or other anti-clotting fluids to prevent clotting on the scaffolding structure. To that end, an anti-clotting coating can be applied to the surface of the scaffolding structure, the sheath and/or the catheter body. A suitable coating, such as a bioactive heparin or heparin-based coating, is available from SurModics, Inc., Eden Prairie, Minn.

The infusion tube may also be used to deliver dye through the distal end of the catheter tip section 14 for fluoroscopy as an aid for navigation and locating position of the catheter. The infusion tube may be made of any suitable material, and is preferably made of polyimide tubing. A preferred infusion tube has an outer diameter of from about 0.032 inch to about 0.036 inch and an inner diameter of from about 0.028 inch to about 0.032 inch.

With reference to FIGS. 2, 3 and 4, a first infusion tube segment 88 extends through the central lumen 18 of the catheter body 12 and terminates in the proximal end of the third lumen 34 of the tip section 14. The distal end of the first infusion tube segment 88 is anchored in the third lumen 34 by polyurethane glue or the like. The proximal end of the first infusion tube segment 88 extends through the control handle 16 and terminates in a luer hub 90 (FIG. 1) or the like at a location proximal to the control handle. A second infusion tube segment 89 (FIG. 3) is provided at the distal end of the third lumen 34 and extends into the fluid passage 35 of the tip electrode 36. The second infusion tube segment 89 is anchored within the third lumen 34 and the fluid passage 35 by polyurethane glue or the like. The second infusion tube segment 89, like the puller wire 42, provides additional support for the tip dome/electrode 36. In practice, fluid may be injected into the first infusion tube segment 88 through the luer hub 90, and flows through the first infusion tube segment 88, through the third lumen 34, through the second infusion tube segment 89 into the fluid passage 35 in the dome/tip electrode 36, and out fluid passage 35 and the branches 48. Again, the fluid passage may have other configurations as desired. For example, the fluid passage 35 may form merely a longitudinal hole that extends out the distal end of the dome 36 or the dome 36 may be porous enough to allow fluids to pass to its outer surface, the interconnecting pores forming the fluid passage.

Figure 3A:
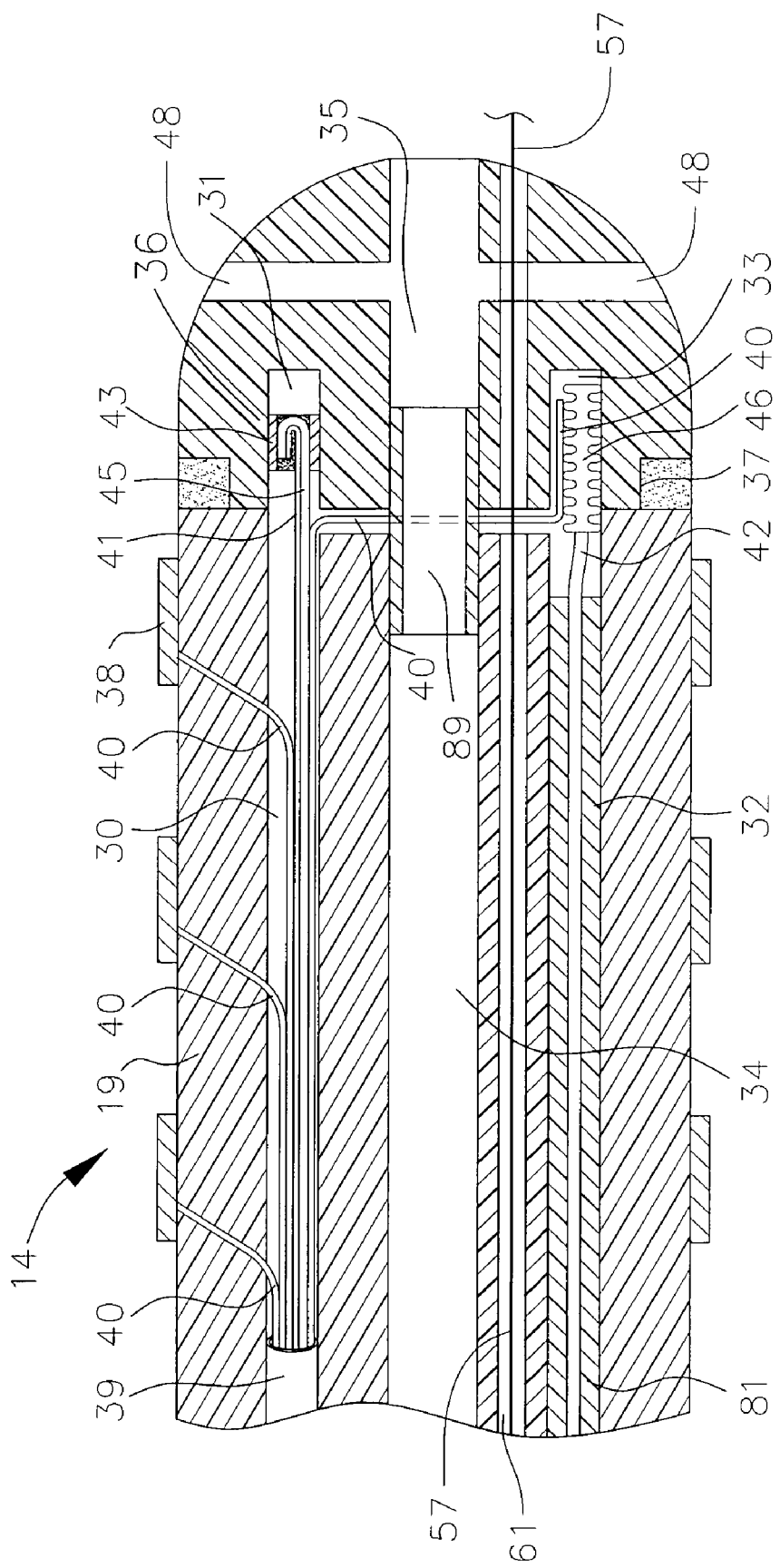
FIG. 3A is a side cross sectional view of an alternative embodiment of the distal end of the tip section.
Figure 4B:
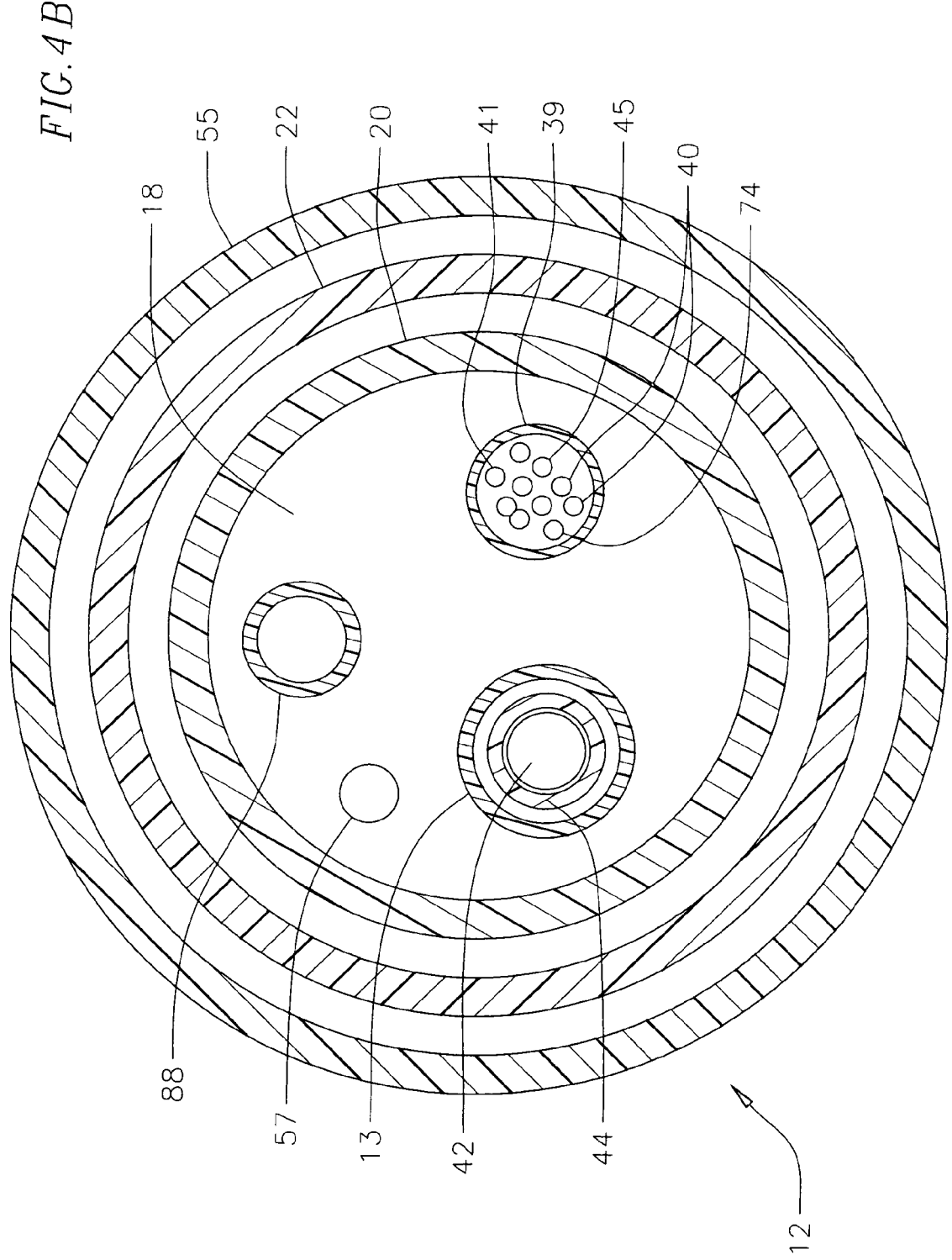
FIG. 4B is a cross sectional view of an alternative embodiment of the catheter body having the guidewire lumen.

It is also contemplated that the fluid passage 35 can receive a guidewire 57 that is front loaded into the catheter 10. As the sheath 55 extends the length of the catheter body 12, the guidewire 57 extends through the fluid passage 35, the third lumen 34 of the tip section 14, the central lumen 18 of the catheter body 12 and the control handle 16 to exit at a location proximal of the proximal end of the sheath 35, for example, out the proximal end of the control handle 16. Alternatively, a guidewire lumen 61 (FIGS. 3A, 4A and 4B) is configured in the dome 36 and the tip section 14 such that the guidewire 57 is front loaded through the dome 36 and fed through the lumen 61 in the tip section 14 and the central lumen 18 of the catheter body 12 to exit out of the control handle 16 at a location proximal of the proximal end of the sheath 35, for example, the proximal end of the control handle 16. In one embodiment, the guidewire lumen has a diameter ranging between about 0.020 inch and about 0.024 inch, and is preferably about 0.021 inch.

Longitudinal movement of the puller wire 42 relative to the catheter body 12, which results in deflection of the tip section 14, is accomplished by suitable manipulation of the control handle 16, including a longitudinally slidable thumbknob 71 (FIG. 1). The degree of deflection of the tip section 14 may range between an A curve and a G curve, preferably E and F curves and more preferably a D curve. Moreover, longitudinal movement of the sheath 55 relative to the catheter body 12 and tip section 14 which results in deployment and recapture of the scaffolding structure 14 is accomplished by suitable manipulations of the control handle 16, including a longitudinally slidable lever 73 that is situated in a longitudinal slot 75 configured in the control handle 16. The proximal end of the sheath 55 may be affixed to a ring that is slidable on a rod extending longitudinally in the control handle. Movement of the proximal end of the sheath 55 is therefore accomplished with direct or indirectly coupling of the ring to the lever 73. As such, the length of the slot 75 limits the distance the sheath 55 can be moved distally and proximally. Control mechanisms and control handles suitable for the present invention include those described in U.S. Pat. No. 6,171,277 and in U.S. application Ser. Nos. 10/820,968, 10/753,666, 09/975,873 and/or 10/175,113, the entire disclosures of which are incorporated herein by reference. Control mechanisms suitable for bidirectional deflection of the catheter include those described in U.S. Pat. No. 6,795,721, the entire disclosure of which is incorporated by reference.

Figure 12:
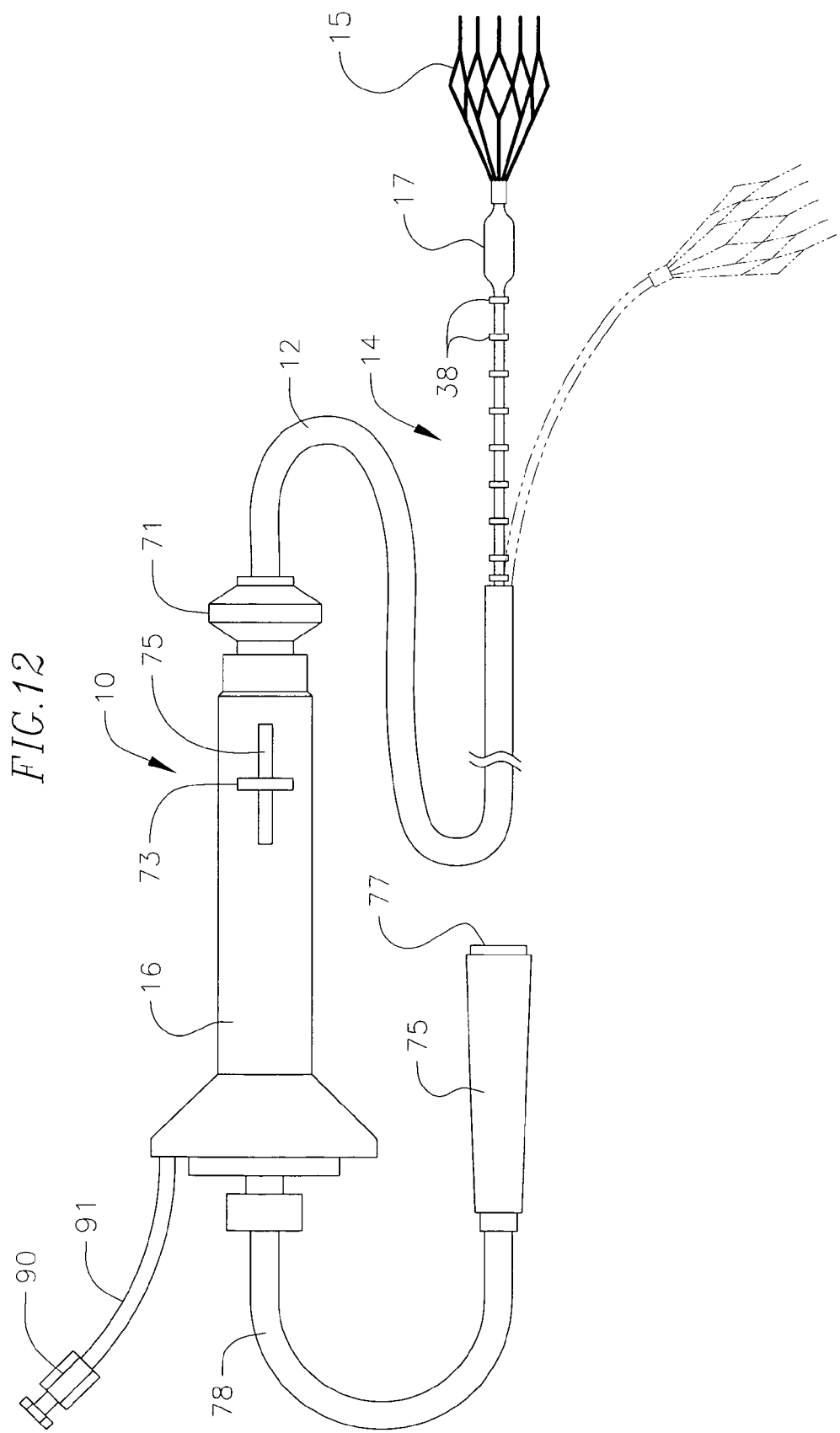
FIG. 12 is a side view of another embodiment of the catheter of the present invention, with the scaffolding structure deployed.
Figure 13:
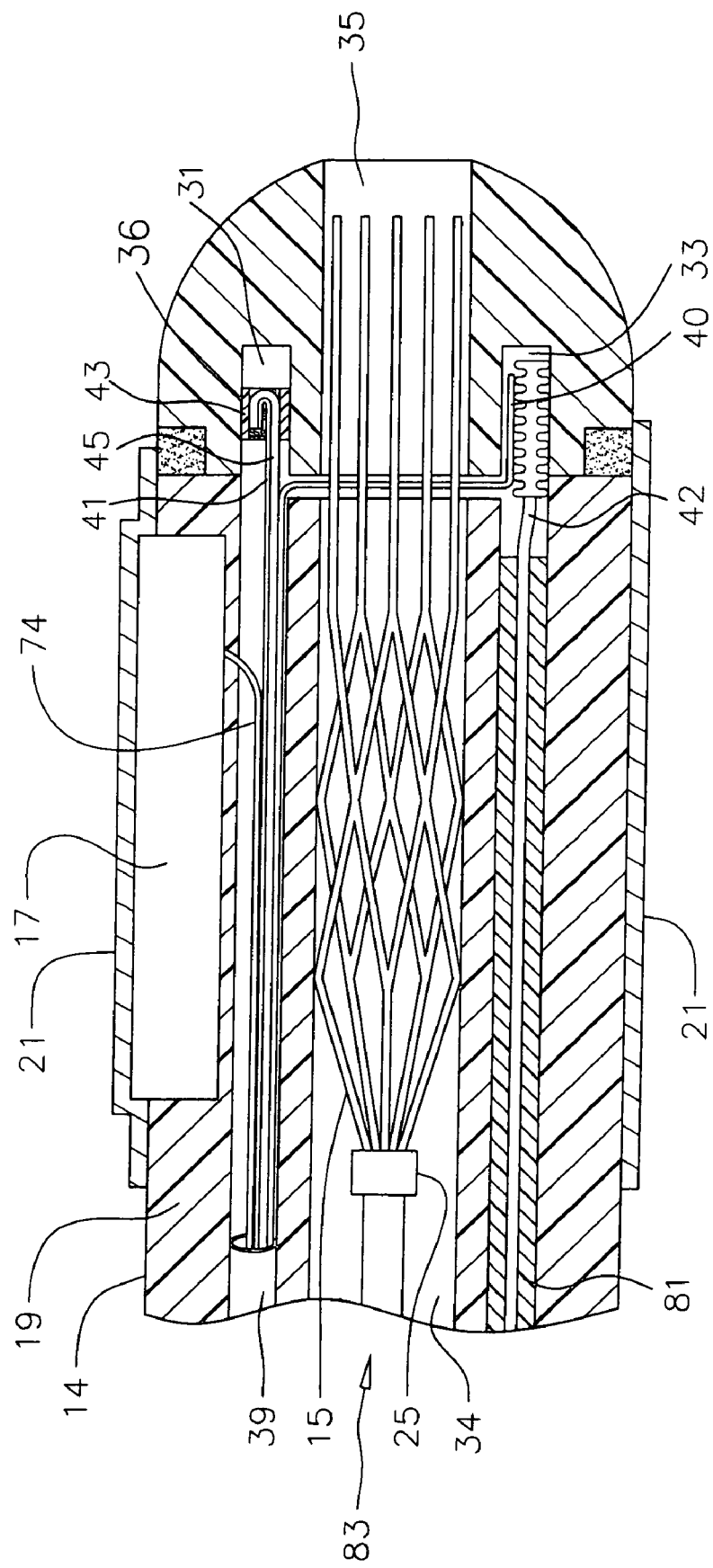
FIG. 13 is a side cross sectional view of the distal end of the tip section of the catheter of FIG. 12, with the scaffolding structure in the recaptured configuration.
Figure 14:
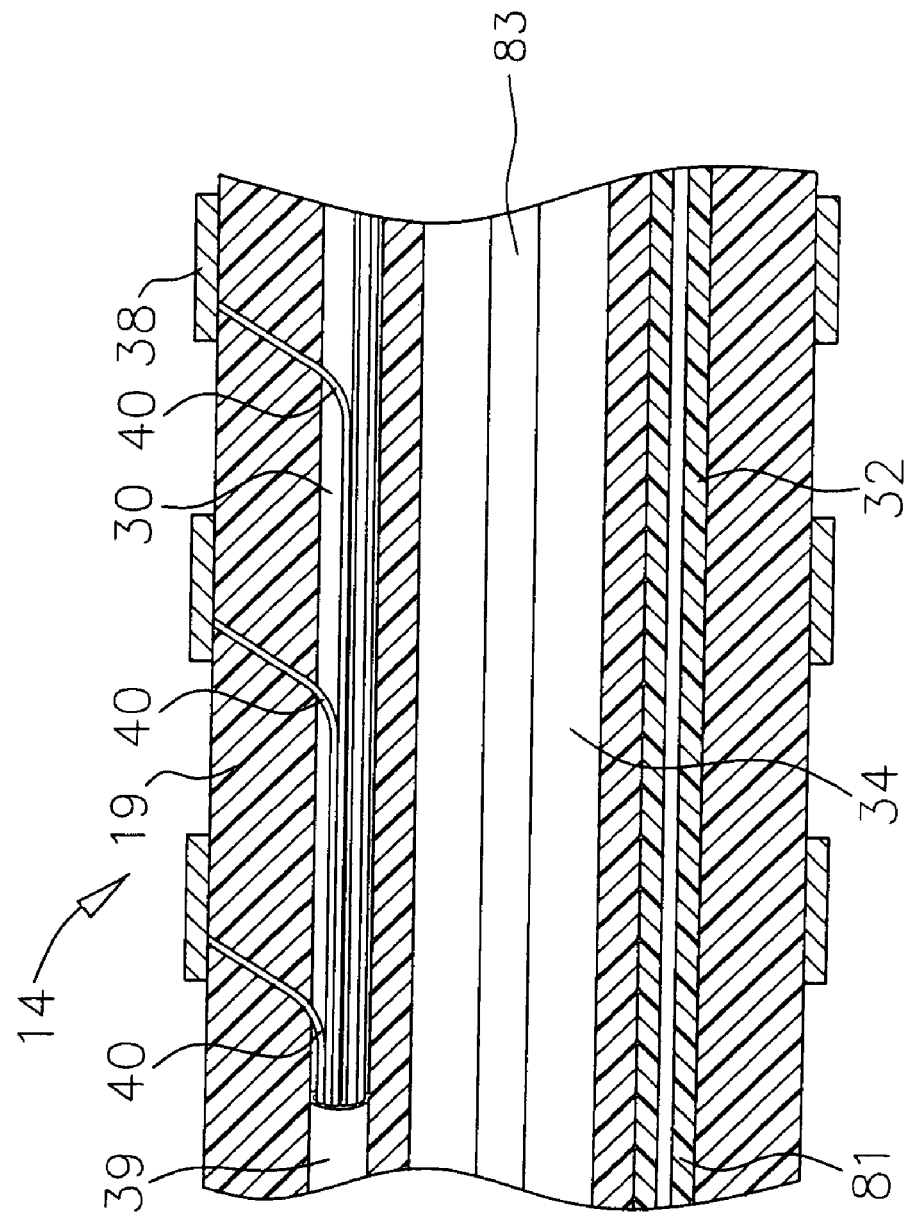
FIG. 14 is a side cross sectional view of the tip section of the catheter of FIG. 12.
Figure 15:
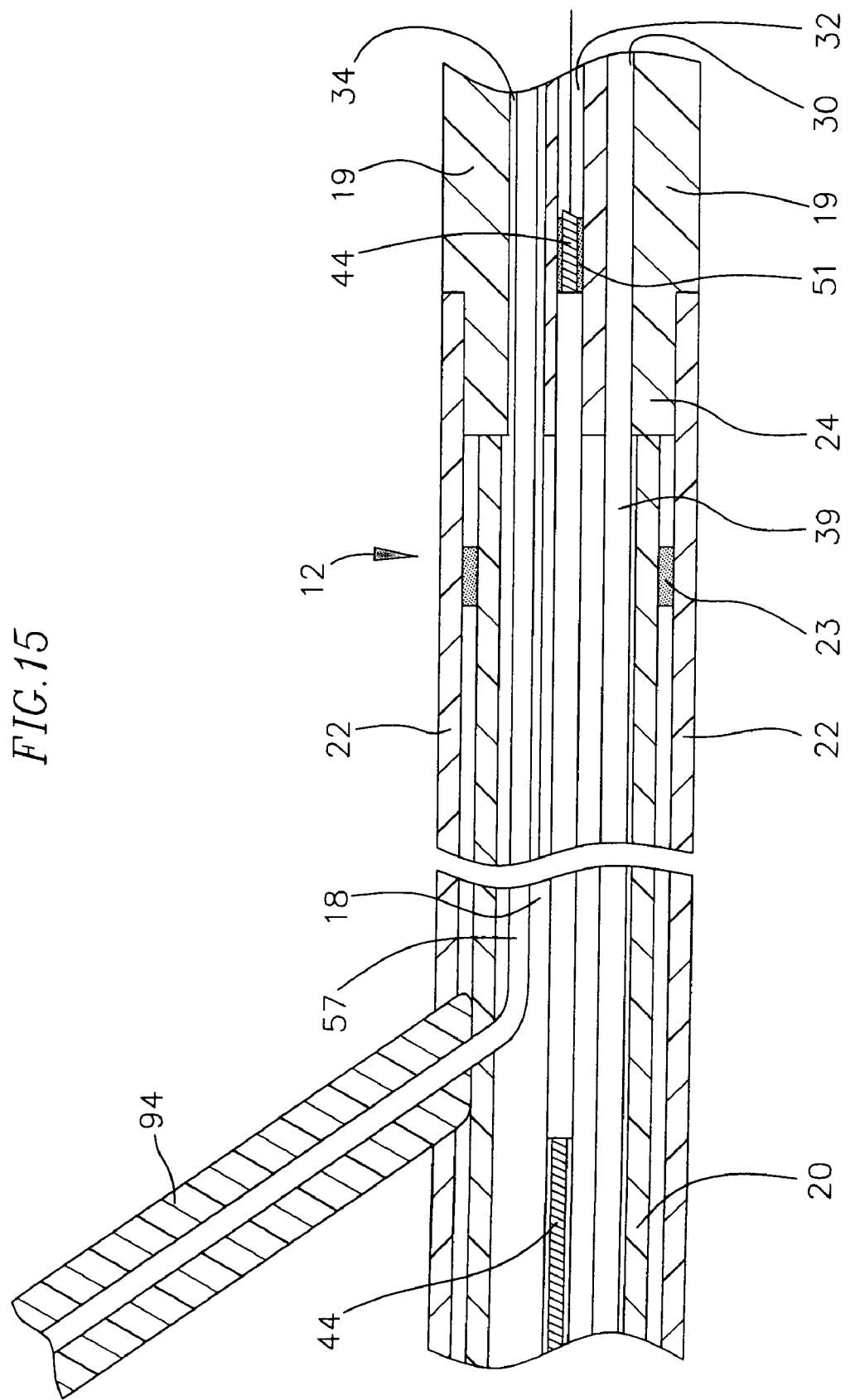
FIG. 15 is a side cross-section view of an embodiment of the catheter body of the present invention with the guidewire exit.

In another preferred embodiment according to the invention, a sheathless catheter 10 is shown in FIGS. 12, 13 and 14, where the scaffolding structure 15 is housed in and deployed from the third lumen 34 of the tip section 14 which is in communication with the axially aligned passageway 35 in the dome. The sensor 17 and the ring electrodes 38 are positioned on the tubing 19 of the tip section 14 and proximal of the distal end of the tip section 14 and dome 36 from which the scaffolding structure 15 is deployed. A second puller wire 83 extends from the control handle 16 through the central lumen 18 of the catheter body 12 and the third lumen 34 of the tip section 14. The proximal end of the scaffolding structure 15 is fixed to the distal end of the second puller wire 83 by the ring 25. It is further contemplated that additional electrophysiology devices can be attached to a closed distal end of the scaffolding structure 15, such as a very flexible wire with a variety of configurations, such as a closed or an open loop, for mapping and tracking applications.

As the second puller wire 83 is moved distally, the scaffolding structure 15 is deployed from the distal end of the tip section 14 and the dome/tip electrode 36 and freely expands to contact and anchor the tip section 14 against the inner walls of a tubular region such as the coronary sinus. The tip section 14, including the proximal sensor and/or the ring electrodes, are consequently stabilized while the scaffolding structure 15 is deployed. As the second puller wire 83 is moved proximally, the scaffolding structure 15 readily collapses and is withdrawn into the passage 35 and central lumen 34. Accordingly, during advancement of the catheter body 12 and tip section 14 in the patient's body, the scaffolding structure 15 is safely housed within the third lumen 34 of the catheter tip section 14. Upon reaching the target site, the second puller wire 83 is moved distally to deploy the scaffolding structure 15 past the distal end of the catheter tip section 14 and dome 36. It is understood by one of ordinary skill in the art that in this embodiment the scaffolding structures with a closed distal end may be preferred over those with an open distal end.

The catheter 10 of FIGS. 12, 13 and 14 may also have a guidewire lumen 61 (see FIG. 3A) to receive a guidewire 57. Since the embodiment of the catheter 10 of FIGS. 12, 13, and 14 is without the outer sheath 55, an exit aperture for the guidewire 57 is provided by an off-axis lumen 94 which may be provided at a location ranging between about 45 cm and 65 cm, and preferably about 55 cm, from the distal end of the tip section 14. The angle offset of the lumen 94 from the longitudinal axis of the catheter body 12 may range between about 30-60 degrees, and preferably about 45 degrees.

As shown in FIG. 6, the reference sensor 17 is connected to a electromagnetic sensor cable 74 within the sheath 39 which extends through in first lumen 30 of the tip section 14 and the central lumen 18 of the catheter body 12, and into the control handle 16. The electromagnetic sensor cable 74 then extends out the proximal end of the control handle 16 within an umbilical cord 78 (FIGS. 1 and 12) to a sensor control module 75 that houses a circuit board (not shown). Alternatively, the circuit board can be housed within the control handle 16, for example, as described in U.S. Pat. No. 5,964,757, entitled "Steerable Direct Myocardial Revascularization Catheter", the disclosure of which is incorporated herein by reference. The electromagnetic sensor cable 74 comprises multiple wires encased within a plastic covered sheath. In the sensor control module 75, the wires of the electromagnetic sensor cable 74 are connected to the circuit board. The circuit board amplifies the signal received from the electromagnetic sensor 17 and transmits it to a computer in a form understandable by the computer by means of the sensor connector 77 at the proximal end of the sensor control module 75, as shown in FIGS. 1 and 12. Suitable electromagnetic sensors for use with the present invention are available available from Biosense Webster, Inc., Irwindale, Calif. and may be described in U.S. Pat. Nos. 5,558,091, 5,443,489, 5,480,422, 5,546,951, 5,568,809, and/or 5,391,199 and/or International Publication No. WO 95/02995, the disclosures of which are incorporated herein by reference.

To use the catheter 10, the patient is placed in a magnetic field generated, for example, by situating under the patient a pad containing coils for generating a magnetic field. The catheter 10 carrying the reference electromagnetic sensor 17 and a second catheter containing a second electromagnetic sensor are advanced into the patient's heart. In particular, the catheter 10 is advanced into the coronary sinus where the thumbknob 71 is used to steer and deflect the catheter tip section 14 into the ostium of the coronary sinus. Once the catheter tip section 14 is inside the coronary sinus, the lever 73 of the control handle 16 is manipulated to deploy the scaffolding structure 15. The amount of movement of the lever 73 (either proximally with the catheter embodiment of FIG. 1, or distally with the catheter embodiment of FIG. 12) depends on the configuration of the tip section 14 as to the relative positioning of the scaffolding structure 15 and the elements proximal thereof. Once deployed, the scaffolding structure 15 self-expands to anchor itself and the adjacent sensor 17 and/or ring electrodes 38 within the coronary sinus against movement caused by blood flow, contractions of the heart muscle and/or respiration.

Each of the sensor 17 and the sensor of the second catheter comprises three small coils that in the magnetic field generate weak electrical signals indicative of their position in the magnetic field. Signals generated by both the relatively fixed reference sensor 17 and the second sensor of the second catheter in the heart are amplified and transmitted to a computer that analyzes the signals and then displays the signals on a monitor. By this method, the precise location of the sensor in the second catheter relative to the reference sensor 17 of the catheter 10 can be ascertained and visually displayed. The reference sensor 17 also enables detection of any displacement of the second catheter that is caused by contraction of the heart muscle.

Using this technology, the physician can visually map a heart chamber when the catheter tip of the second catheter tip is advanced into a heart chamber until contact is made with the heart wall. This position is recorded and saved. The catheter tip is then moved to another position in contact with the heart wall and again the position is recorded and saved. This procedure is repeated until a three-dimensional image of the heart chamber is achieved. A preferred mapping system includes a second catheter comprising multiple electrodes and an electromagnetic sensor.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter for use in or near a coronary sinus of a human heart, comprising:
   an elongated catheter body having proximal and distal ends;
   a tip section fixedly attached at the distal end of the catheter body, said tip section having proximal and distal ends and carrying a plurality of electrodes, an electromagnetic sensor and a scaffolding structure having proximal and distal ends and adapted to assume an expanded configuration and a collapsed configuration, the proximal end of the scaffolding structure being fixedly attached to the tip section and the distal end of the scaffolding structure being freely slidable along the tip section;
   a sheath extending along the catheter body and having a length such that its distal end is adapted to reach the distal end of the scaffolding structure; and
   a control handle at the proximal end of the catheter body, the control handle adapted to deflect the tip section and to move the sheath proximally and distally over the scaffolding structure.

2. A catheter of claim 1, wherein the scaffolding structure remains generally stationary during movement of the sheath.

3. A catheter of claim 1, wherein the scaffolding structure is a generally spherical shape.

4. A catheter of claim 1, wherein the scaffolding structure is a generally ovoid shape.

5. A catheter of claim 1, wherein the scaffolding structure is proximal of the sensor.

6. A catheter of claim 1, wherein the scaffolding structure is distal of the sensor.

7. A catheter of claim 1, wherein the control handle comprises a slidable thumbknob configured to deflect the tip section.

8. A catheter of claim 1, wherein the control handle comprises a slidable lever configured to move the sheath distally and proximally.

9. A catheter of claim 1, wherein the scaffolding structure is a generally peanut shape.

10. A catheter of claim 1 wherein the scaffolding structure is a generally synaptic shape.

11. A catheter for use in or near a tubular region of a human heart, comprising:

an elongated catheter body having proximal and distal ends;

a tip section fixedly attached at the distal end of the catheter body, said tip section having proximal and distal ends and carrying a plurality of electrodes, an electromagnetic sensor and a scaffolding structure having proximal and distal ends and adapted to assume an expanded configuration and a collapsed configuration, the proximal end of the scaffolding structure being fixedly attached to the tip section and the distal end of the scaffolding structure being freely slidable along the tip section;

a sheath extending along the catheter body and having a length such that its distal end is adapted to reach the distal end of the scaffolding structure; and a control handle at the proximal end of the catheter body, the control handle adapted to deflect the tip section and to move the sheath proximally and distally over the scaffolding structure, wherein the scaffolding structure is in the collapsed configuration when surrounded circumferentially by the sheath and wherein the scaffolding structure is radially expanded when it is distal of the sheath,for stabilizing the tip section in the tubular region.

12. The catheter of claim 11, wherein the sensor is a reference electromagnetic sensor.

13. The catheter of claim 11, wherein the plurality of electrodes ranges between eight and ten.

14. The catheter of claim 11, wherein the catheter body comprises an infusion tube in communication with a lumen in the tip section, the infusion tube and the lumen adapted to pass a fluid out the distal end of the tip section.

15. The catheter of claim 14, wherein the infusion tube and the lumen are adapted to pass a fluid having anti-clotting properties out the distal end of the tip section.

16. The catheter of claim 14, wherein the infusion tube and the lumen are adapted to pass a dye out the distal end of the tip section.

17. The catheter claim 11 wherein the catheter body and tip section each comprises a lumen in communication with each other and adapted to receive a guidewire therethrough.

* * * * *